US007801343B2

United States Patent
Unal et al.

(10) Patent No.: US 7,801,343 B2
(45) Date of Patent: Sep. 21, 2010

(54) METHOD AND APPARATUS FOR INNER WALL EXTRACTION AND STENT STRUT DETECTION USING INTRAVASCULAR OPTICAL COHERENCE TOMOGRAPHY IMAGING

(75) Inventors: Gozde Unal, West Windsor, NJ (US); Yan Yang, Atlanta, GA (US); Gregory G. Slabaugh, Princeton, NJ (US); Tong Fang, Morganville, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 993 days.

(21) Appl. No.: 11/555,806

(22) Filed: Nov. 2, 2006

(65) Prior Publication Data

US 2007/0167710 A1    Jul. 19, 2007

Related U.S. Application Data

(60) Provisional application No. 60/740,367, filed on Nov. 29, 2005.

(51) Int. Cl.
*G06K 9/00* (2006.01)
*A61B 5/05* (2006.01)
(52) U.S. Cl. ............................ 382/128; 600/407
(58) Field of Classification Search .............. 382/128, 382/129, 130, 131, 132, 133, 134; 378/4, 378/8, 21–27, 101, 140, 901; 600/407, 410, 600/425, 427, 480, 489, 490, 500, 505; 623/903, 623/916, 921; 128/920, 922

See application file for complete search history.

(56) References Cited

U.S. PATENT DOCUMENTS 7,184,150 B2 *   2/2007   Quadling et al. ............ 356/602
7,397,935 B2 *   7/2008   Kimmel et al. ............. 382/128

OTHER PUBLICATIONS

Chan, T. et al., "An Active Contour Model Without Edges," Department of Mathematics, University of California, Los Angeles, pp. 141-151 (1999).
Malladi, R. et al., "Shape Modeling with Front Propagation: A Level Set Approach," IEEE Transactions on Pattern Analysis and Machine Intelligence, 17:2 pp. 158-175 (1995).
Caselles, V. et al., "Geodesic Active Contours," International Journal of Computer Vision, 22:2 pp. 61-79 (1997).

* cited by examiner

*Primary Examiner*—Abolfazl Tabatabai

(57) ABSTRACT

A method and apparatus for automatically detecting stent struts in an image is disclosed whereby the inner boundary, or lumen, of an artery wall is first detected automatically and intensity profiles along rays in the image are determined. In one embodiment, detection of the lumen boundary may be accomplished, for example, by evolving a geometric shape, such as an ellipse, using a region-based algorithm technique, a geodesic boundary-based algorithm technique or a combination of the two techniques. Once the lumen boundary has been determined, in another embodiment, the stent struts are detected using a ray shooting algorithm whereby a ray is projected outward in the OCT image starting from the position in the image of the OCT sensor. The intensities of the pixels along the ray are used to detect the presence of a stent strut in the image.

33 Claims, 7 Drawing Sheets

METHOD AND APPARATUS FOR INNER WALL EXTRACTION AND STENT STRUT DETECTION USING INTRAVASCULAR OPTICAL COHERENCE TOMOGRAPHY IMAGING

This patent application claims the benefit of U.S. Provisional Application No. 60/740,367, filed Nov. 29, 2005, which is hereby incorporated by reference herein in its entirety.

BACKGROUND OF THE INVENTION

The present invention relates generally to optical coherence tomography imaging techniques and, more particularly, to stent strut detection using such techniques.

Coronary artery diseases, such as atherosclerosis, are a leading cause of death in the industrialized world. In particular, atherosclerotic plaques may cause narrowing or blockage of the coronary arteries, resulting in reduced blood supply to the heart tissue, which may sometimes lead to serious results such as heart attacks. Medical imaging techniques have greatly assisted the diagnosis and treatment of such coronary artery diseases. For example, coronary X-ray angiography, computed tomography angiography (CTA), magnetic resonance angiography (MRA), intravascular ultrasound (IVUS), and optical coherence tomography (OCT), have all been used to, for example, identify the different constituents of atherosclerotic plaques in the coronary arteries. Of these techniques, CTA and MRA are desirable since they are non-invasive imaging techniques, however, the low resolution of these techniques has limited their ability to resolve the different constituent parts of atherosclerotic plaques.

OCT is able to achieve much higher resolution than CTA and MRA. However, this technique requires invasive catheterization. More particularly, OCT is a medical imaging technology that is functionally similar to ultrasound (IVUS), but relies on infrared light waves instead of sound. As one skilled in the art will recognize, since the frequency of light is much higher than the frequency of sound waves, OCT systems can produce images having a far greater resolution than ultrasound images. In coronary artery imaging application, the resolution of OCT techniques (on the order of 10 µm) can typically not only differentiate between typical constituents of atherosclerotic plaques, such as lipid, calcium, and fibrous tissue, but can also resolve the thin fibrous cap that is thought to be responsible for plaque vulnerability. OCT systems use, for example, a compact diode light source that may be illustratively interfaced with a catheter, endoscope, laparoscope, and/or a surgical probe using well-known optical fiber techniques to image an anatomical feature of a patient. In operations, OCT systems measure the echo time delay and intensity of reflected/backscattered light from, for example, an anatomical feature of a patient, and use this light to produce images that are two- or three-dimensional data sets.

FIG. 1 shows an illustrative OCT sensor that may be used in accordance with an embodiment of the present invention to image one or more anatomical features of a patient, such as the contours of the coronary arteries of the patient. Referring to FIG. 1, sensor 100 is, for example, connected to a diode light source via line 101 that is used to transmit optical signals to and from sensor 100. Sensor 100 is illustratively passed through a catheter 102 that is, for example, transparent to optical or infrared frequencies or another frequency useful in imaging an anatomical feature. In accordance with an embodiment of the present invention, catheter 102 is illustratively first inserted into an anatomical region to be imaged. Then, sensor 100 is passed through the catheter to a desired initial position, for example to an initial position within a coronary artery to be imaged. One skilled in the art will recognize that, in one illustrative embodiment, sensor 100 may already be present within catheter 102 when the catheter is inserted. Once the sensor 100 is in its initial position, an optical signal of a desired frequency, such as at an optical or infrared frequency, is then passed to the sensor 100 via line 101. The resulting signal is then transmitted to device 103 which is, illustratively, a mirror (e.g., a micro mirror) or a prism that functions to direct the signal in direction 307 toward surface 108 (i.e., the surface to be imaged). When the signal reaches surface 108, a portion of the light is reflected in direction 109. When this reflected portion reaches device 103, it is reflected back in direction 110 along line 101 to image processing equipment for processing the collected data into an image. Techniques for processing image data collected by an OCT sensor are well known. Accordingly, such techniques will not be further described herein.

In many uses, such as when the inner surface of a coronary artery is to be imaged, it is desirable to obtain a cross section image of the artery. In such an implementation, sensor 100 is capable of being rotated in directions 105 about axis 111. Accordingly, as the sensor is rotated, the signal reflected by device 103 will rotate around the surface of the artery at the location of the sensor, and image data is collected around the entire diameter of the surface. Thus, as one skilled in the art will recognize, for each position of sensor 100 within an artery, rotating the sensor will produce a cross section image of the artery at that position. Then, according to the present embodiment, in order to obtain an image of the entire artery, the sensor 100 can be retracted along a known path, and data can be collected for a plurality of cross section images of the artery at different positions.

When a full or partial blockage of coronary arteries is diagnosed, various medical procedures may be used to attempt to re-open the blocked arteries. For example, one such procedure, known as percutaneous transluminal coronary angioplasty (PTCA) may be used to open the blocked artery. In many instances a stent is implanted after the angioplasty to keep the artery open and prevent restenosis (regrowth of the plaque). As one skilled in the art will recognize, stents are small metal scaffolds either made from bare metal or coated with drug to inhibit restenosis. Drug-coated stents can also be used to significantly reduce the occurrence of neointimal hyperplasia (NIH), which is a potential complication resulting from the use of stents whereby the inner layer of the blood vessel thickens, possibly causing the closing of the newly opened blood vessel.

SUMMARY OF THE INVENTION

The present inventors have recognized that the distribution of stent struts within an artery may affect the ability of a drug-coated stent to deliver a desired drug concentration to various portions of the artery. More particularly, if the strut distribution is nonuniform, the resulting nonuniform distribution of the respective drug within the artery may also affect the magnitude of NIH after stent implantation. Previous methods used to potentially detect the distribution of stent struts typically involved acquiring IVUS or OCT images and then manually processing those images to identify individual struts. However, such manual processing was not always accurate and required a significant time investment. Thus, the present inventors have recognized that it would be desirable to be able to automatically detect stent struts in an image such as an image obtained from OCT imaging techniques.

The present inventors have invented a method and apparatus for automatically detecting stent struts in an image obtained, for example, via OCT imaging techniques whereby the inner boundary of the artery wall is first detected automatically. One skilled in the art will recognize that the inner boundary of such an artery is also referred to as the lumen boundary of the artery. As such, the term lumen boundary will be used interchangeably herein to refer to the inner surface or wall of an artery. In one embodiment, detection of the lumen boundary may be accomplished, for example, by evolving a geometric shape, such as an ellipse, using either a region-based algorithm technique, a geodesic boundary-based algorithm technique or a combination of the two techniques. Once the lumen boundary has been determined, in another embodiment, the stent struts are detected using a ray shooting algorithm whereby a ray is projected outward in the OCT image starting from the position in the image of the OCT sensor. The intensities of the pixels along the ray are used to detect the presence of a stent strut in the image. Alternatively, in another embodiment, the OCT generated cross section image of the artery is transformed into a rectangular coordinate system and the intensity of the pixels in at least one direction are used to detect stent struts. In this way, the arrangement and distribution of stents may be automatically and accurately determined.

These and other advantages of the invention will be apparent to those of ordinary skill in the art by reference to the following detailed description and the accompanying drawings.

DETAILED DESCRIPTION

Figure 2:
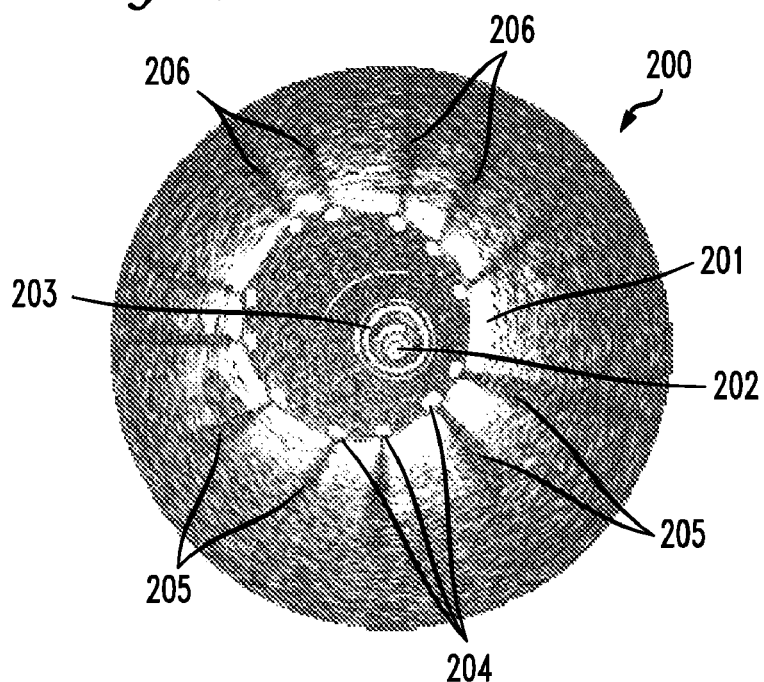
FIG. 2 shows an image of a coronary artery obtained via OCT imaging and stent struts within the artery.

FIG. 2 shows a cross section image 200 showing an artery 201, which is for example a coronary artery in which a stent has been inserted. Image 200 is illustratively an image obtained via OCT scanning using optical or infrared light transmitted by sensor 202 that has been inserted into artery 201 using catheter 203. As one skilled in the art will recognize, the relatively bright portion of the image represents the wall of artery 201. FIG. 2 also shows cross section images of the struts 204 of a stent that has been inserted into the artery. Shadows, such as shadows 205, result when the stent blocks the optical or infrared signal originating from sensor 202. As discussed above, it is desirable to be able to locate the struts 204 in the image accurately but prior manual methods for identifying such struts were not accurate and typically took extensive time to perform. Accordingly, the present inventors have invented a method and apparatus for automatically identifying the struts in an image, such as struts 204 in image 200.

In order to identify the presence and locate the position of stent struts in an image, the present inventors have recognized that it is desirable to first detect the lumen boundary of the artery into which a stent has been inserted. This is desirable since the stent strut cross sections in the image will be located in relatively close proximity to the inner boundary of the artery. Therefore, in accordance with one embodiment, such identification of the lumen boundary is illustratively achieved by segmenting the image using an active contour. As one skilled in the art will recognize, such active contours are contours that start from an initial estimated position and then are caused to move in a desired direction, here, for example, in the direction of the lumen boundary. More particularly, an initial contour is placed on the image within the cross sectional area of the artery and the contour is then mathematically subjected to various forces that evolve it over the image, thus moving the contour towards the pixels in the image that represent the lumen boundary. Upon completion of the contour evolution, the contour is substantially in the position and shape of the lumen boundary.

Figure 3:
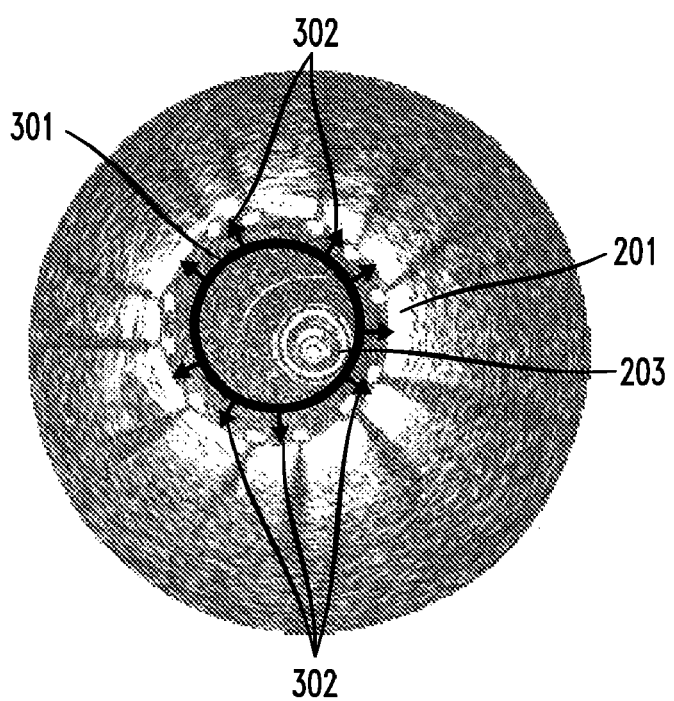
FIG. 3 shows how an illustrative ellipse contour can be evolved to detect a lumen boundary of the artery of FIG. 2.

FIG. 3 illustrates how such a contour line may start at an initial estimated position and be evolved using known image segmentation techniques to identify the lumen boundary. Specifically, as discussed above, FIG. 3 shows an initial estimate contour line 301 inside the cross section image of the artery 201. The present inventors have recognized that is desirable to use an ellipse as the initial contour line, since such a shape is a good approximation of the lumen boundary. However one skilled in the art will recognize that many different geometric shapes and even free-form shapes may be used as an initial contour line with equally advantageous results. The initial contour line 301 is illustratively placed in the image in a way such that the OCT imaging sensor and/or the catheter in which it is placed is within the contour line. As one skilled in the art will recognize, this is desirable because the mathematical techniques used to evolve contour lines are frequently a function of the intensity of the pixels in the image. Placing the initial position of the contour line outside the catheter will ensure that the flow algorithm used will not misidentify the catheter (or other artifacts in the image) as the lumen boundary. As one skilled in the art will recognize, since the catheter is always in the center of the image, in one embodiment a preprocessing step may be used to detect and remove the catheter artifact lines, which are typically distinctive circular bright patterns around the catheter. Once the initial position of the contour line is set, then well-known mathematical techniques are applied to evolve the contour line iteratively such that the contour line moves outward in directions 302 and, ultimately, to a position conforming substantially to the inner wall of artery 201 in the image.

As one skilled in the art will recognize, many different well-known mathematical flow functions can be used advantageously to achieve the evolution of a contour line. As discussed above, an ellipse contour line is desirable as an initial contour line in such an evolution since it is, in general, a good approximation of the lumen boundary. In OCT images that contain stent struts and corresponding trailing shadows (such as shadows 205 in FIG. 2), ellipses are especially advantageous in accurately identifying the lumen boundary. In accordance with an embodiment of the present invention, a combined region and boundary-based segmentation is used to evolve the ellipse contour line. As one skilled in the art will recognize, such a combined approach takes in to account both edge information associated with the contour line, as well as regional statistical information of the image to evolve the ellipse contour to the lumen boundary. Such an approach is merely illustrative. As one skilled in the art will recognize, instead of using such a combined evolution algorithm, it is also possible to use a boundary-based or region based algorithm individually to achieve advantageous results in different embodiments.

In order to perform the aforementioned evolution, a point on a two-dimensional ellipse parameterized by $p \in [0, 2\pi)$ can be defined according to the expression $$p = \begin{pmatrix} a\cos(p) \\ b\sin(p) \end{pmatrix}.$$

The translation vector of such an ellipse may be expressed as $t = \begin{pmatrix} d \\ e \end{pmatrix}$, and the rotation matrix of the ellipse can be expressed as $$R = \begin{pmatrix} \cos(\theta_e) & \sin(\theta_e) \\ -\sin(\theta_e) & \cos(\theta_e) \end{pmatrix}.$$

As a result, the parameterization of an elliptical contour line in two dimensions can be defined by the expression:

$$\epsilon(p) = a \begin{pmatrix} \cos(\theta_e) \\ -\sin(\theta_e) \end{pmatrix} \cos(p) + b \begin{pmatrix} \sin(\theta_e) \\ \cos(\theta_e) \end{pmatrix} \sin(p) + \begin{pmatrix} d \\ e \end{pmatrix}. \quad \text{(Equation 1)}$$

Using the ellipse parameterization of Equation 1, a generic region-based energy function may be defined by the expression:

$$E(C) = \int_{C_{in}} f(x) dx + \int_C ds \quad \text{(Equation 2)}$$

where $f = f_{in} - f_{out}$ and $f_{in}$ and $f_{out}$ represent region descriptors inside and outside the contour C respectively. For example, a piecewise constant model can be utilized by choosing $f = (I - \text{mean}_{in})^2 - (I - \text{mean}_{out})^2$. Typically, a regularization on the unknown contour C is included as provided by the second term of Equation 2, when the active contour being utilized is not a parametric contour. Utilizing the ellipse parameterization of Equation 1, then, the variation of the energy in Equation 2 with regard to ellipse parameters $\lambda^i \in \{a, b, d, e, \theta_e\}$, $i = 1, \ldots, 5$ yields a region-based gradient flow given by the expression:

$$\frac{d\lambda^i}{dt} = \int f(x) \left\langle \frac{\partial \epsilon(p)}{\partial \lambda^i}, N \right\rangle dp \quad \text{(Equation 3)}$$

describing the evolution of the ellipse for the energy of Equation 2. In Equation 3, values for $$\frac{\partial \epsilon(p)}{\partial \lambda^i}$$

are given for each parameter according to the expressions:

$$\frac{\partial \epsilon(p)}{\partial a} = \begin{pmatrix} \cos(\theta_e) \\ -\sin(\theta_e) \end{pmatrix} \cos(p) \quad \text{(Equation 4)}$$

$$\frac{\partial \epsilon(p)}{\partial b} = \begin{pmatrix} \sin(\theta_e) \\ \cos(\theta_e) \end{pmatrix} \sin(p) \quad \text{(Equation 5)}$$

$$\frac{\partial \epsilon(p)}{\partial d} = \begin{pmatrix} 1 \\ 0 \end{pmatrix}, \frac{\partial \epsilon(p)}{\partial e} = \begin{pmatrix} 0 \\ 1 \end{pmatrix} \quad \text{(Equation 6)}$$

and $$\frac{\partial \epsilon(p)}{\partial \theta_e} = \begin{pmatrix} -a\sin(\theta_e)\cos(p) + b\cos(\theta_e)\sin(p) \\ -a\cos(\theta_e)\cos(p) - b\sin(\theta_e)\sin(p) \end{pmatrix}. \quad \text{(Equation 7)}$$

Also, in Equation 3, the variable N is defined by the expression:

$$N(p) = \begin{pmatrix} a\sin(\theta_e)\sin(p) + b\cos(\theta_e)\cos(p) \\ a\cos(\theta_e)\sin(p) - b\sin(\theta_e)\cos(p) \end{pmatrix},$$

and represents the normal vector of the ellipse.

As discussed above and as one skilled in the art will recognize, the gradient flows of Equation 3 represent a region-based approach for evolving an ellipse contour to, for example, the lumen boundary of an artery. Alternatively, in a boundary-based approach, for a contour $C(t) = \epsilon(t)$ which is an ellipse once again having parameters $\lambda^i$, the geodesic energy of the contour can be defined by the expression:

$$E(\epsilon) = \int_0^1 \Phi \|\epsilon_p\| dp, \quad \text{(Equation 8)}$$

where $\Phi$ is a weighting function which is usually designed to slow down the evolution of the contour at high image gradients (e.g., where pixels in proximity to each other have a significantly different pixel intensity). Here, for example, $\Phi = -\|\nabla(G*I)\|^2$, where G is a Gaussian smoothing filter. Thus, the variation of the energy in Equation 8 with regard to ellipse parameters $\lambda^i$ yields a boundary-based gradient flow defined by the expression:

$$\frac{\partial \lambda^i}{\partial t} \int_0^1 \left\langle \nabla \Phi, \frac{\partial \epsilon}{\partial \lambda^i} \right\rangle \|\epsilon_p\| dp - \int_0^1 \Phi \left\langle \frac{\partial \epsilon}{\partial \lambda^i}, T_p \right\rangle dp \quad \text{(Equation 9)}$$

describing the evolution of the ellipse for the energy of Equation 8.

As discussed herein above, in order to improve the accuracy of the evolution of the ellipse to the position of the lumen of an artery, the present inventors have recognized it is desirable to combine the region and boundary-based gradient flows. In order to combine the region-based flow of Equation 3 and the boundary-based flow of Equation 9, a weighting parameter $\alpha$ is used to balance the two terms. The resulting combination of these two flow equations can be defined by the expression:

$$\frac{\partial \lambda^i}{\partial t} = \alpha \bigg( \int_0^1 \bigg\langle \nabla \Phi, \frac{\partial \varepsilon}{\partial \lambda^i} \bigg\rangle \|\varepsilon_p\| dp -$$
$$\int_0^1 \Phi \bigg\langle \frac{\partial \varepsilon}{\partial \lambda^i}, T_p \bigg\rangle dp \bigg) + (1 - \alpha) \int_0^1 f(x) \bigg\langle \frac{\partial \varepsilon}{\partial \lambda^i}, N \bigg\rangle \|\varepsilon_p\| dp.$$

(Equation 10)

As one skilled in the art will recognize in light of the forgoing, the curvature-like term of Equation 10 of $$\bigg\langle \frac{\partial \varepsilon}{\partial \lambda^i}, T_p \bigg\rangle$$

can be eliminated since an ellipse is always convex. Accordingly, a final ellipse evolution equation that combines the region-based and boundary-based gradient flows can be defined by the expression:

$$\frac{\partial \lambda^i}{\partial t} = \int_0^1 \bigg\langle \frac{\partial \varepsilon}{\partial \lambda^i}, [\alpha \nabla \Phi + (1 - \alpha) f(x) N] \bigg\rangle \|\varepsilon_p\| dp.$$

(Equation 11)

Thus, Equation 11 describes the gradient flow that can be used to determine the evolution of an ellipse to segment an image and determine the lumen boundary of an artery. The results of such an evolution can be seen with reference to FIG. 4 where, illustratively, ellipse 401 has evolved to the position of the lumen boundary of artery wall 201.

Once the lumen boundary has been determined as described above, in accordance with another embodiment of the present invention, the locations of the cross section images of the stent struts are determined. More particularly, in accordance with this embodiment, rays are generated, originating from the position of the OCT sensor, such as sensor 202 in FIG. 2, and are propagated in all directions outward from the OCT sensor. As was discussed above, stent struts typically block the propagation of the infrared signal transmitted by the OCT sensor and, as a result, leave a shadow, such as shadows 205 in FIG. 2, on the opposite side of the stent cross section in the image generated by the OCT scanning process. Thus, referring to FIG. 2, the intensity profile of the pixels in image 200 along a ray passing through a stent strut cross section, and then propagating into the shadow will be detectably different from the intensity profile of the pixels in the image along a ray passing only through the artery wall with no stent strut/shadow along the path of the ray.

In detecting the stent struts, it is desirable to weaken the affects of far-field light attenuation. Such a weakening may be accomplished by compensating the image intensity by multiplying each intensity profile with an exponential function of the form:

$$I^* = (1 + e^{(x/k)}) I$$

(Equation 12)

where I* is the compensated intensity, x is the distance from the origin to the current pixel, and k is the compensation coefficient that is adjusted to raise the intensity around the vessel wall. The intensity profile along each ray-shooting direction is then illustratively smoothed by an averaging filter, and normalized to be between [0, 1].

Figure 5A:
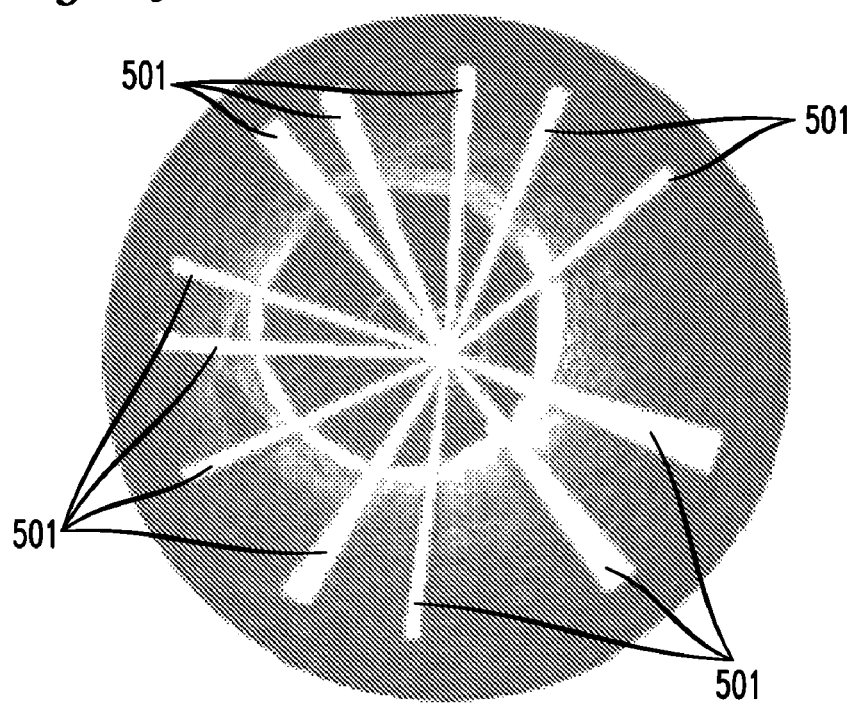
FIG. 5A shows how rays can be propagated to detect stent struts using image intensity profiles along each ray.

In order to determine which rays pass through the stent struts and which pass through the vessel wall, it can be observed that those that pass through the struts have a narrow bright peak in the intensity profiles, while those pass through the vessel wall have a wide flat peak. A threshold of the peak width is selected to distinguish between the two types of rays, and those who have a narrow peak are labeled as strut-rays. FIG. 5A shows the rays 501 that were determined according to this method as passing through stent struts. To locate the stent struts precisely, a search may be conducted for bright peaks along each of the strut-rays. To avoid false detection resulting from the catheter or artifacts inside the lumen boundary area, the search for bright peaks can be initiated from a relatively small distance from the lumen boundary area, here illustratively approximately ~0.2 mm (20 pixels) inside the lumen segmentation result, and only search for bright peaks from this point outward along the ray.

Figure 4:
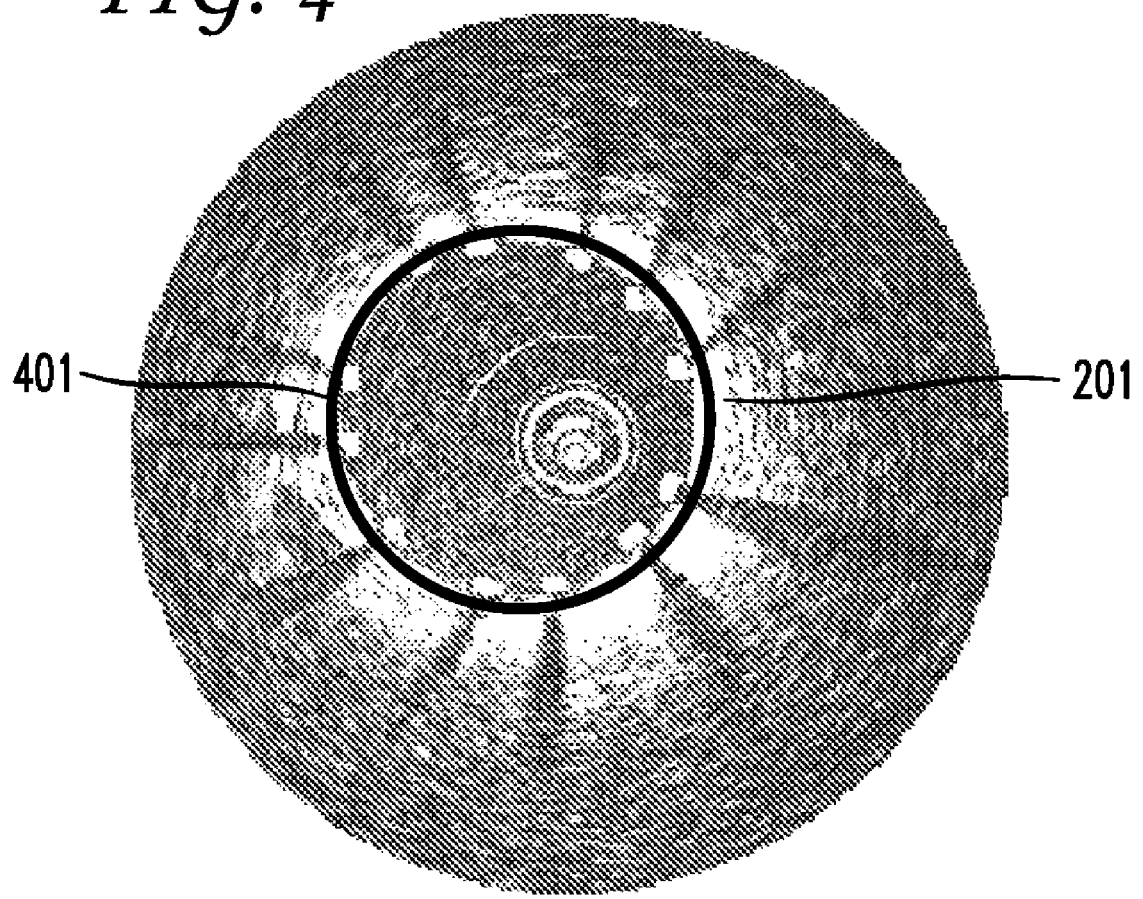
FIG. 4 shows the ellipse contour of FIG. 3 after the contour has been evolved to the position of the lumen boundary.
Figure 5B:
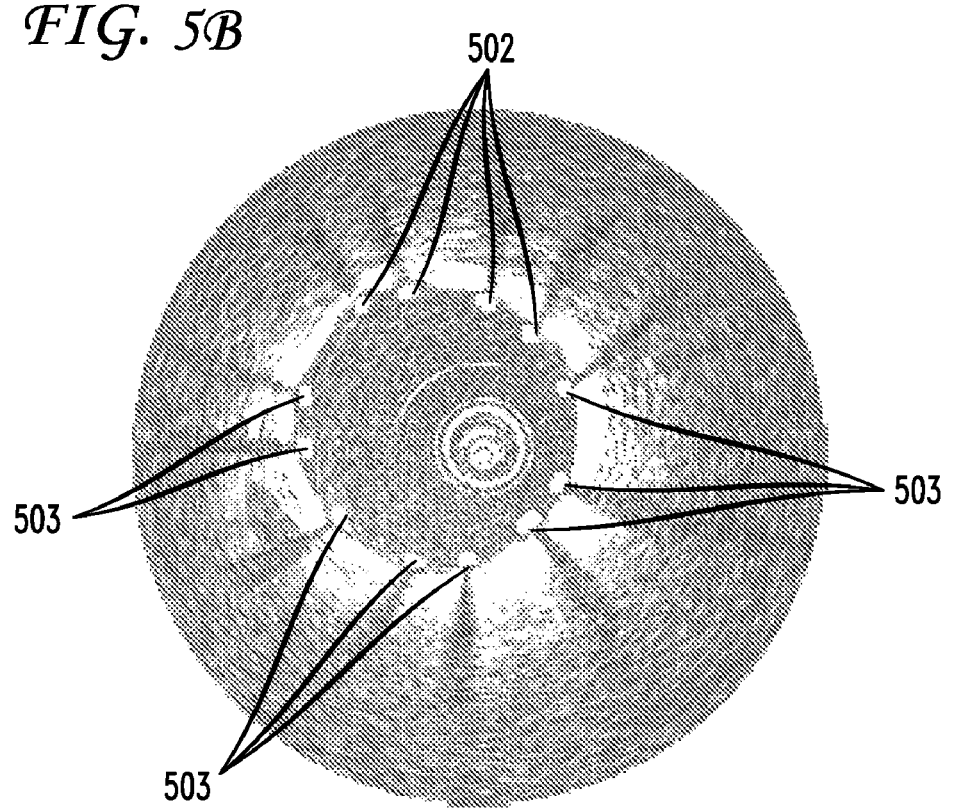
FIG. 5B shows cross section images of the stent struts as detected according to the image intensity profiles along the rays of FIG. 5A.

Typically, as one skilled in the art will recognize in light of the foregoing, the bright peak that corresponds to a stent strut is visible and detectable. However, sometimes invisible struts are present for which only trailing shadows are detectable (but not the bright peaks). In such a case, the location of the strut can be approximated at the location where the ray intersects the lumen boundary corresponding to that strut shadow. For example, referring once again to FIG. 2, shadows 206 are readily apparent and detectable via examining the intensity profile along rays originating from the OCT sensor. However, the stent strut itself is either not visible or of low visibility for each of shadows 206. Accordingly, once the lumen boundary has been detected, as described herein above and as represented by contour 401 in FIG. 4, the intersection of the rays that correspond to shadows 206 in FIG. 2 with the contour 401 in FIG. 4 are detected and a stent strut is identified as being located at that position. The result of such a detection of stent struts is shown in FIG. 5B. Specifically, referring to that figure, struts 503 are identified by detecting a bright peak in intensity corresponding to the stent strut cross section, followed by a shadow on the opposite side of the stent strut from the OCT sensor. Struts 502, on the other hand, are detected by detecting a shadow, but no strut, and then determining the intersection of the rays in this area of shadow with the contour line 401 of FIG. 4. In this way, the position of stent struts within an artery can be identified.

Figure 6:
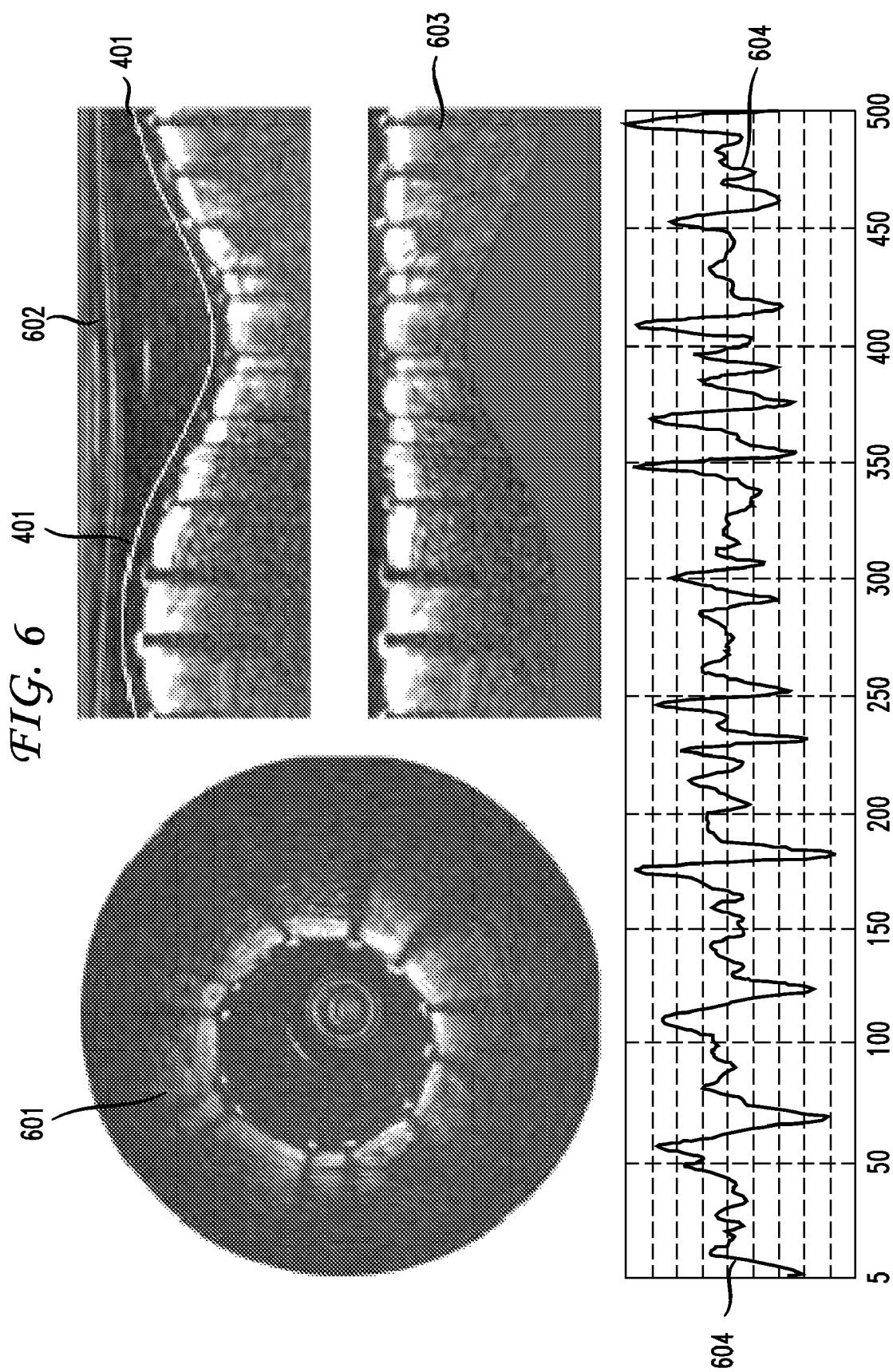
FIG. 6 shows how an image can be transformed into a rectangular coordinate system and an image intensity profile associated with the transformed image can be used to detect stent struts.

The forgoing ray-shooting algorithm can accurately identify stent struts for most cases when there are a limited number of struts and clearly defined trailing shadows are present. However, this method only takes into account the radial information along the rays. Therefore, when the struts are very narrow or the shadows are vague, the ray-shooting algorithm could potentially fail to find the strut-rays. Therefore, in accordance with another embodiment of the present invention, the present inventors have recognized that it may be desirable to review the intensity profile in a direction tangential to the vessel wall in an attempt to detect the large intensity gradient that typically corresponds to the shadows. Such a tangential detection can be accomplished by transforming the cross section image of the artery and stent struts to a rectangular coordinate system and then rectifying the transformed map by using the ellipse segmentation contour discussed above. FIG. 6 shows such a transformed image from an original image 601 (which is, for example, the same image as in FIGS. 2, 3, 4, 5A and 5B) to a rectangular coordinate system view 602, which is then rectified into view 603 so that contour 401 is disposed along a horizontal axis. Then, once this rectified image is defined, the sum of the intensity along the vertical direction is determined and plotted into a one dimensional profile 604, which represents a gradient map associated with the rectified image 603. By detecting large peaks in the profile 604, in conjunction with the low intensity sum in the shadow regions, additional strut shadows can be detected that were potentially missed by the ray-shooting algorithm. One skilled in the art will recognize that, since the dimensions of the artery and stent struts are distorted in view 603, this complimentary method will not provide the size of the struts. However, even if the struts detected using this technique are very small in size, the size of the struts in the physical domain may, in one embodiment, be estimated by an inverse transformation of the size information by reversing the rectification of the contour and the rectangular transform.

Once the determination has been made according to the forgoing methods as to which rays pass through stent struts, it is then possible to determine strut distribution within the artery. Specifically, struts can be illustratively grouped by, for example, determining which adjacent rays pass through a strut and grouping them as corresponding to a single strut. Once all such struts have been identified, it then possible to determine the size (width) of each strut, angles and distances between strut pairs, and the total number of struts presenting in the image. Such information makes it possible to identify the specific strut distribution and, as a result, assess the potential risk of NIH in a patient.

One skilled in the art will also recognize that the forgoing methods can be used even in the case where the stents are not newly implanted, such as would be the case when a follow-up study of the stent strut distribution is involved. In such a case, the stent struts typically are not disposed directly on the inner surface of the artery but, instead there is typically a layer of NIH on top of the struts. Accordingly, if the foregoing methods are applied directly, the results may not be accurate since the ellipse lumen segmentation result could be too far away from the actual stent boundary. Thus, the present inventors have recognized that, in order to get a better approximation of the stent boundary, an edge detection operator (such as the well-known Roberts operator) may be applied to the image and the outer boundary edges with an ellipse. Starting from this ellipse, one skilled in the art will recognize how to apply the forgoing evolution techniques with such an operator to detect struts in arteries in which NIH is present.

Figure 1:
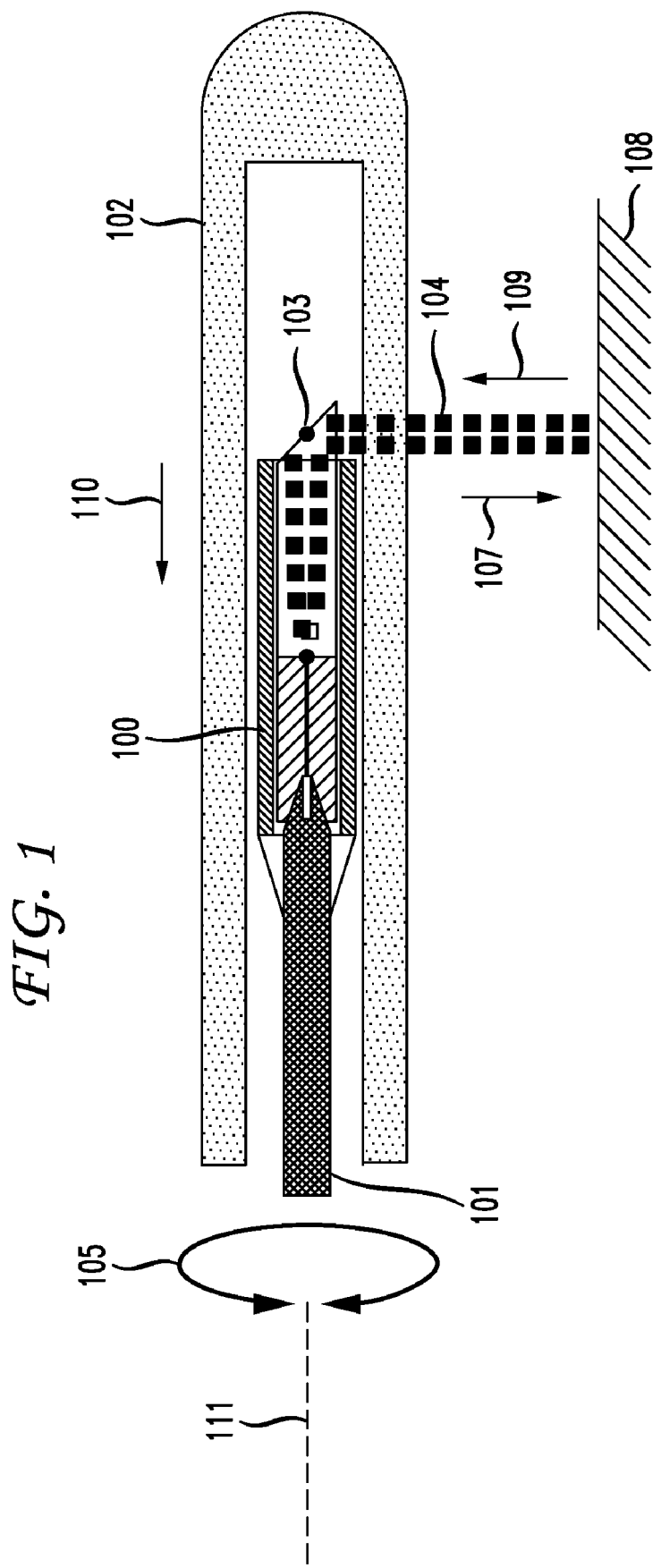
FIG. 1 shows an illustrative optical coherence tomography (OCT) imaging sensor useful in accordance with the principles of the present invention.
Figure 7:
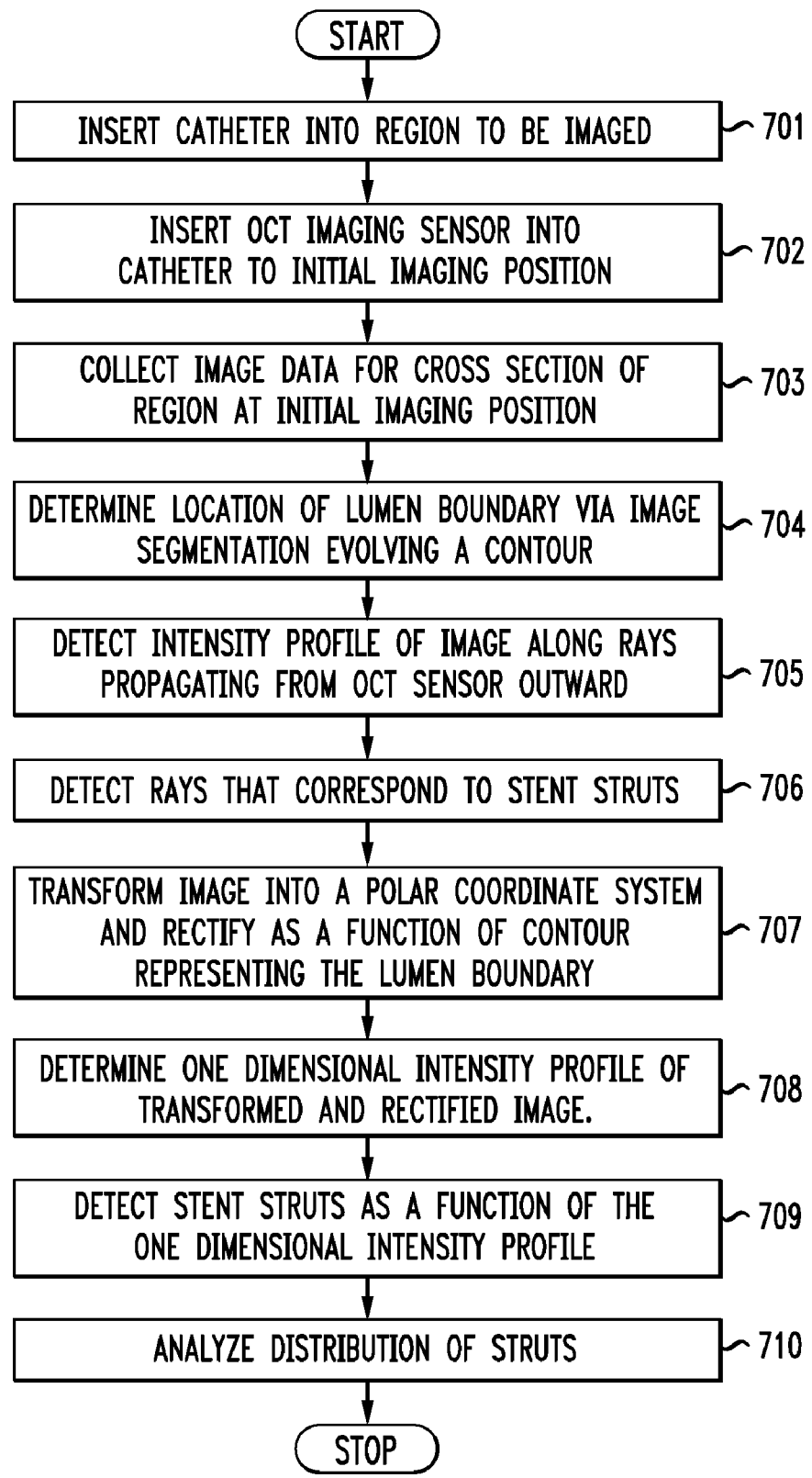
FIG. 7 is a flow chart showing the steps of a method in accordance with an embodiment of the present invention.

FIG. 7 is a flow chart showing the illustrative steps of a method in accordance with an embodiment of the present invention. Referring to that figure, at step 701, an illustrative catheter is inserted into a region, such as a region of coronary artery to be imaged. Then, at step 702, an OCT imaging sensor, such as sensor 100 of FIG. 1, is inserted into the catheter. As discussed above, one skilled in the art will recognize that, in another embodiment, the sensor may already be contained within the catheter when the catheter is inserted into the region to be imaged. At step 703, image data is collected using well-known OCT techniques. At step 704, a location of the lumen boundary of the artery is determined using, for example, image segmentation techniques. As discussed herein above, such techniques may be boundary-based, region based, or a combination boundary/region-based technique. Next, at step 705, an image intensity profile of the pixels along each of a plurality of rays originating from, illustratively, an imaging sensor (such as an OCT sensor) is determined. Then, at step 706, the location of stent struts are determined as a function of these image intensity profiles. In order to detect any stent struts that are not readily visible in the image, at step 707, the image is then transformed into a rectangular coordinate system and is rectified as a function of the detected lumen boundary profile. Then, at step 708, a second image intensity profile is then determined in a direction tangential to the artery wall and, at step 709, any additional stent struts are located as a function of this second image intensity profile. Finally, at step 710, the strut distribution is assessed.

Figure 8:
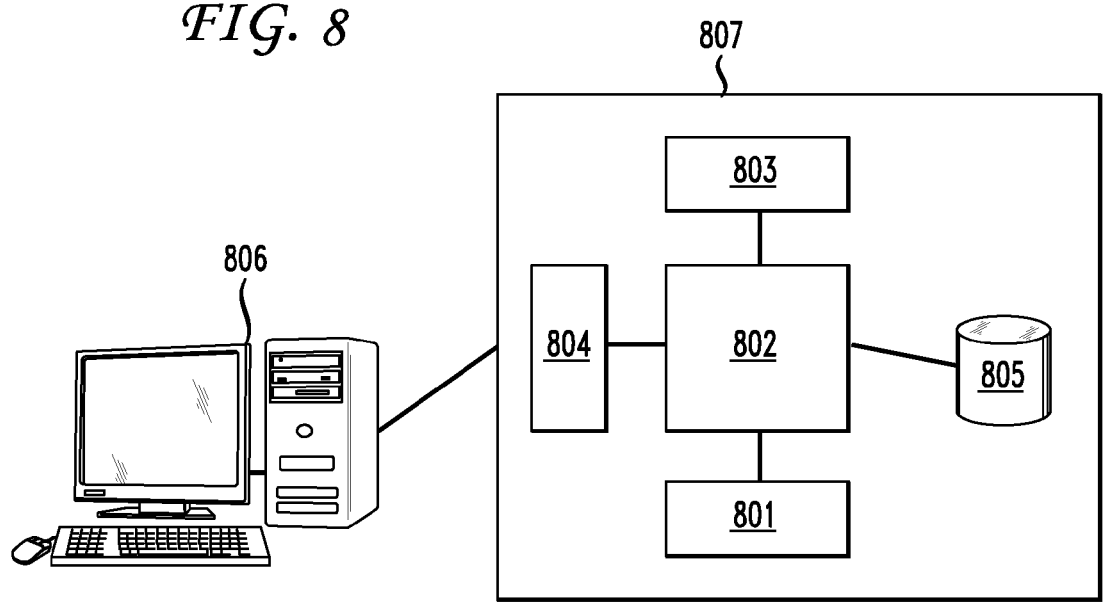
FIG. 8 shows a computer adapted to perform the illustrative steps of the method of FIG. 7 as well as other functions associated with the imaging of a coronary artery and the identification of stents in such an image in accordance with the embodiments of the present invention.

The foregoing embodiments are generally described in terms of manipulating objects, such as images, cross sections, rays and shadows associated with detecting stent struts inside an artery. One skilled in the art will recognize that such manipulations may be, in various embodiments, virtual manipulations accomplished in the memory or other circuitry/hardware of an illustrative image collection and processing system. Such an image collection and processing system may be adapted to perform these manipulations, as well as to perform various methods in accordance with the above-described embodiments, using a programmable computer running software adapted to perform such virtual manipulations and methods. An illustrative programmable computer useful for these purposes is shown in FIG. 8. Referring to that figure, an image collection and processing system 807 is implemented on a suitable computer adapted to receive, store and transmit data such as the aforementioned image and position information associated with imaging the interior of a coronary artery and detecting stent struts. Specifically, illustrative image collection and processing system 807 may have, for example, a processor 802 (or multiple processors) which controls the overall operation of the registration system 807. Such operation is defined by computer program instructions stored in a memory 803 and executed by processor 802. The memory 803 may be any type of computer readable medium, including without limitation electronic, magnetic, or optical media. Further, while one memory unit 803 is shown in FIG. 8, it is to be understood that memory unit 803 could comprise multiple memory units, with such memory units comprising any type of memory. Image collection and processing system 807 also comprises illustrative modem 801 and network interface 804. Image collection and processing system 807 also illustratively comprises a storage medium, such as a computer hard disk drive 805 for storing, for example, data and computer programs adapted for use in accordance with the principles of the present invention as described hereinabove. Finally, image collection and processing system 807 also illustratively comprises one or more input/output devices, represented in FIG. 8 as terminal 806, for allowing interaction with, for example, a technician or database administrator. One skilled in the art will recognize that registration system 807 is merely illustrative in nature and that various hardware and software components may be adapted for equally advantageous use in a computer in accordance with the principles of the present invention.

One skilled in the art will also recognize that the software stored in the computer system of FIG. 7 may be adapted to perform various tasks in accordance with the principles of the present invention. In particular, such software may be graphical software adapted to import surface cross section image information from anatomical structures, for example the image information generated from the direct scanning of an ear canal as described above. In addition, such software may allow for selective editing of that information in a way that allows the identification and evolution of contour lines, as described above, or that permits a user to form or remove rays propagating across an image. The software of a computer-based system such as image collection and processing system 707 may also be adapted to perform other functions, which will be obvious in light of the teachings herein. All such functions are intended to be contemplated by these teachings.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for locating a stent strut in a cross section image of a vessel comprising:
   identifying, by a processor, in said image an inner boundary of said vessel, the step of identifying comprising the steps of:
      placing a contour in an initial position in said image; and
      moving an edge of said contour toward said inner boundary until said contour reaches said inner boundary;
   detecting, by the processor, a location of said stent strut as a function of a plurality of intensity profiles associated with a plurality of rays in said image;
   transforming said image into a rectangular coordinate system to create a transformed image;
   rectifying said transformed image as a function of said contour;
   determining a sum of intensities of a plurality of pixels along a desired direction in said image; and
   identifying said location of said stent as a function of said sum of intensities.

2. The method of claim 1 further comprising:
   prior to said step of placing, detecting a catheter artifact in said image, said catheter artifact associated with a catheter in said vessel.

3. The method of claim 1 further comprising the step of:
   determining said contour has reached said inner boundary as a function of an intensity of a plurality of pixels in said image.

4. The method of claim 1 wherein said edge of said contour is moved according to an evolution method.

5. The method of claim 4 wherein said evolution method comprises a boundary-based evolution method.

6. The method of claim 4 wherein said evolution method comprises a region-based evolution method.

7. The method of claim 4 wherein said evolution method comprises a combined boundary and region-based evolution method.

8. The method of claim 1 wherein said step of detecting comprises identifying an intensity profile for each ray in said plurality of rays, each of said rays originating from a position of a sensor in said image.

9. The method of claim 8 wherein said sensor is an optical coherence tomography sensor.

10. The method of claim 8 wherein said intensity profile comprises a profile of the intensity of pixels along each ray.

11. The method of claim 10 further comprising:
    determining whether each ray in said plurality of rays passes through a stent strut as a function of said intensity profile.

12. An apparatus for locating a stent strut in a cross section image of a vessel comprising:
    means for identifying in said image an inner boundary of said vessel, the means for identifying comprising:
       means for placing a contour in an initial position in said image; and
       means for moving an edge of said contour toward said inner boundary until said contour reaches said inner boundary;
    means for detecting a location of said stent strut as a function of a plurality of intensity profiles associated with a plurality of rays in said image;
    means for transforming said image into a rectangular coordinate system to create a transformed image;
    means for rectifying said transformed image as a function of said contour;
    means for determining a sum of intensities of a plurality of pixels along a desired direction in said image; and
    means for identifying said location of said stent as a function of said sum of intensities.

13. The apparatus of claim 12 further comprising:
    means for detecting a catheter artifact in said image prior to identifying said inner boundary, said catheter artifact associated with a catheter in said vessel.

14. The apparatus of claim 12 further comprising:
    means for determining said contour has reached said inner boundary as a function of an intensity of a plurality of pixels in said image.

15. The apparatus of claim 12 further comprising means for moving said edge of said contour according to an evolution method.

16. The apparatus of claim 15 wherein said evolution method comprises a boundary-based evolution method.

17. The apparatus of claim 15 wherein said evolution method comprises a region-based evolution method.

18. The apparatus of claim 15 wherein said evolution method comprises a combined boundary and region-based evolution method.

19. The apparatus of claim 12 wherein said means for detecting comprises means for identifying an intensity profile for each ray in said plurality of rays, each of said rays originating from a position of a sensor in said image.

20. The apparatus of claim 19 wherein said sensor is an optical coherence tomography sensor.

21. The apparatus of claim 19 wherein said intensity profile comprises a profile of the intensity of pixels along each ray.

22. The apparatus of claim 21 further comprising:
    means for determining whether each ray in said plurality of rays passes through a stent strut as a function of said intensity profile.

23. A nontransitory computer readable medium comprising computer program instructions which, when executed by a processor, perform the steps of a method for locating a stent strut in a cross section image of a vessel, said steps comprising:
    identifying in said image an inner boundary of said vessel, the step of identifying comprising the steps of:
       placing a contour in an initial position in said image; and
       moving an edge of said contour toward said inner boundary until said contour reaches said inner boundary;
    detecting a location of said stent strut as a function of a plurality of intensity profiles associated with a plurality of rays in said image;
    transforming said image into a rectangular coordinate system to create a transformed image;
    rectifying said transformed image as a function of said contour;
    determining a sum of intensities of a plurality of pixels along a desired direction in said image; and
    identifying said location of said stent as a function of said sum of intensities.

24. The nontransitory computer readable medium of claim 23 further comprising computer program instructions defining the step of:

prior to said step of placing, detecting a catheter artifact in said image, said catheter artifact associated with a catheter in said vessel.

25. The nontransitory computer readable medium of claim 23 further comprising computer program instructions defining the step of:
determining said contour has reached said inner boundary as a function of an intensity of a plurality of pixels in said image.

26. The nontransitory computer readable medium of claim 23 further comprising computer program instructions defining the step of moving said edge of said contour according to an evolution method.

27. The nontransitory computer readable medium of claim 26 wherein said evolution method comprises a boundary-based evolution method.

28. The nontransitory computer readable medium of claim 26 wherein said evolution method comprises a region-based evolution method.

29. The nontransitory computer readable medium of claim 26 wherein said evolution method comprises a combined boundary and region-based evolution method.

30. The nontransitory computer readable medium of claim 23 wherein said computer program instructions defining the step of detecting comprises computer program instructions for identifying an intensity profile for each ray in said plurality of rays, each of said rays originating from a position of a sensor in said image.

31. The nontransitory computer readable medium of claim 30 wherein said sensor is an optical coherence tomography sensor.

32. The nontransitory computer readable medium of claim 30 wherein said intensity profile comprises a profile of the intensity of pixels along each ray.

33. The nontransitory computer readable medium of claim 32 further comprising computer program instructions defining the step of:
determining whether each ray in said plurality of rays passes through a stent strut as a function of said intensity profile.

* * * * *